United States Patent [19]

Dragmen, Sr.

[11] Patent Number: 4,715,591
[45] Date of Patent: Dec. 29, 1987

[54] PATIENT SUPPORT FOR RADIATION IMAGING

[75] Inventor: Kenneth J. Dragmen, Sr., South Euclid, Ohio

[73] Assignee: Picker International, Inc., Cleveland, Ohio

[21] Appl. No.: 850,021

[22] Filed: Apr. 10, 1986

[51] Int. Cl.$^4$ .............................................. A61G 13/00
[52] U.S. Cl. ..................................... 269/322; 378/209
[58] Field of Search ................................ 269/322–328; 108/27, 143; 312/190.4; 378/209, 177; 5/425, 424, 193

[56] References Cited

U.S. PATENT DOCUMENTS

| | | | |
|---|---|---|---|
| 1,797,717 | 3/1931 | Coates | 108/27 |
| 2,492,541 | 12/1949 | Stanitz | 108/27 |
| 3,643,604 | 2/1972 | Jones et al. | 108/143 |
| 3,916,203 | 10/1975 | Norgren . | |
| 3,967,333 | 7/1976 | Boyd | 5/424 |
| 3,997,792 | 12/1976 | Conrad et al. | 5/425 |
| 4,197,465 | 4/1965 | Schneider . | |
| 4,506,872 | 3/1985 | Westerberg et al. | 269/322 |
| 4,578,835 | 4/1986 | Vrzalik | 269/328 |

OTHER PUBLICATIONS

Picker International Product Brouchure, *Vector The Exam-Driven R & F system*, 10/83.

Primary Examiner—Robert C. Watson
Attorney, Agent, or Firm—Timothy B. Gurin

[57] ABSTRACT

A radiographic/fluoroscopic X-ray system is disclosed employing a new and improved apparatus for supporting a patient under examination. The system includes a table assembly comprising a main support structure and a patient support member. The patient support member is movably mounted to the main support structure while maintaining a clearance space therebetween. A guard means, mounted to one end of the patient support member is provided to discourage inadvertent placement of a patient's fingers in the clearance space. The guard means is comprised of rigid or semi-rigid material and extends above the clearance space and beyond the end of the patient support member. The guard means defines a space for finger placement which is remote from the clearance space.

5 Claims, 10 Drawing Figures

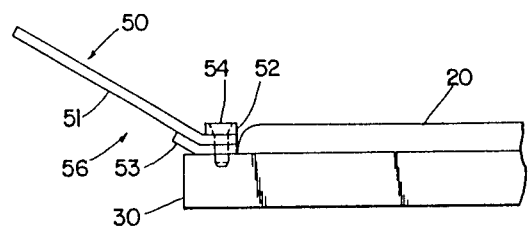
Fig. 6
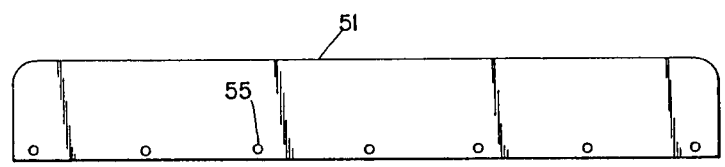
Fig. 7
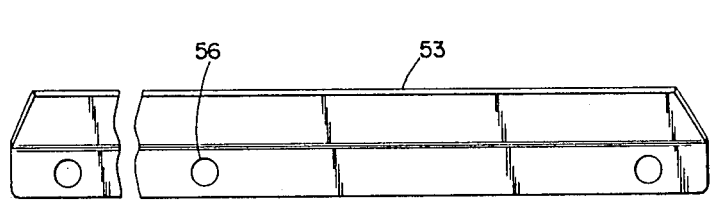 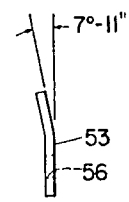
Fig. 8A      Fig. 8B
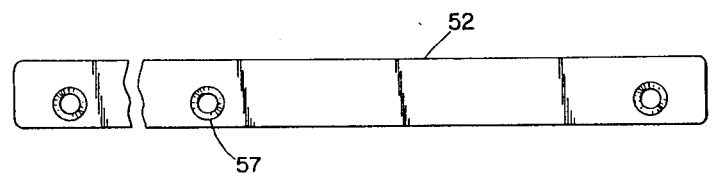
Fig. 9

PATIENT SUPPORT FOR RADIATION IMAGING

DESCRIPTION 1. Technical Field

This invention relates generally to the field of radiation imaging, and more particularly to medical diagnostic radiography employing a new and improved method and apparatus for supporting a subject under examination.

2. Background Art

Conventional radiography and fluoroscopy is a well known art. Conventional radiographic and fluoroscopic (R&F) X-ray systems typically comprise an X-ray table upon which a subject under examination is placed, a source of radiation for propagating X-rays through the subject under examination, an imaging system to convert a pattern of X-radiation eminating from the subject into a corresponding visible light image, a viewing device to display the light image and a spotfilmer for making a film record of the viewed image.

In tiltable type X-ray tables a flat topped elongated table body is pivotally connected to a base or pedestal so that it can be tilted in either direction from its normal position in which the patient-supporting top surface is horizontal. The table body pivots about an axis parallel to its top and perpendicular to it length. In so-called 90/90 tables, the table body is tiltable in either direction 90° from the horizontal. The tilting permits examination of the patient in any angular position between these two extremes. Other tables have a body which is tiltable in one direction from the horizontal to a 90° position and in the other direction to a so-called Trendelenburg position wherein the angle of tilt is limited to an angle of 45° or less from the horizontal.

Such table assemblies typically include a tower assembly which is movably carried by the table body. The tower assembly is carried in a path transverse to the longitudinal extent of the table body by a carriage. The carriage is also movable longitudinally relative to the table body along two rails mounted in the table body. The X-ray source is mounted to the carriage and is housed in the table body. The tower assembly also supports radiation sensing devices such as the spotfilmer and imaging system. The radiation sensing devices are movable with respect to the table assembly in a vertical direction. The imaging system typically includes an image intensifier tube and associated viewing medium for viewing the image intensifier tube output.

The spotfilmer is commonly supported by the tower assembly in spaced relation above a patient examining surface defined by the X-ray table top and in alignment with the X-ray source. The combination of the carriage and tower assembly permit the spotfilmer and imaging system to move in the transverse, longitudinal and vertical directions with respect to the table body.

The X-ray source is mounted to the carriage such that the longitudinal alignment of the source with the radiation sensing devices is maintained during movement along the entire table body length.

An example of one such tiltable X-ray table can be found in U.S. Pat. No. 4,197,465 issued to Schneider, owned by the present assignee and which is expressly incorporated herein by reference.

The three rectilinear paths of travel described above permit the spotfilmer/imaging system combination to be moved to any selected position over the table top and to any selected distance from the top within the limits of the respective paths of travel.

The table top employed in such a system is commonly movable with respect to the table body. Two-way tops and four-way tops are frequently used. A two-way top provides for two-way motion along the longitudinal extent of the table body. A four-way top provides for two-way motion along the longitudinal extent of the table body plus two-way motion in a path transverse to the longitudinal extent. The table top is comprised of a rigid metal frame covered by a radiolucent material such as a plastic laminate.

In operation, the patient undergoing an examination is placed on the table top typically in a prone position. The movable top is adjusted to precisely position the patient with respect to the X-ray tube and imaging systems.

To insure that interference between the table top and table body does not occur during top movement, a clearance space is provided between the table top and table body. It is desirable to keep this space at a minimum, but due to tolerances associated with the componentry provided for table top motion, a gap in the order of 0.5 inches is typical.

Because of the various table top and table body motions that may occur during a patient examination, patients lying on the table top surface may feel insecure or unstable and may grasp a secure structure for balance. If the patient is placed on the table top in a prone, face-down position, the patient frequently brings his/her hands up above his/her head and may find an end of the table top a convenient location to place his/her hands. Grasping the end of the table top in this manner may cause inadvertent placement of fingers in the clearance space between the table top and table body. If further patient positioning is necessary and the table top is moved, particularly in the longitudinal direction, the patient's fingers may interfere with the relative motion of the table top with respect to the table body.

It is therefore an object of this invention to overcome the above referenced problems and others by providing an improved patient support structure.

SUMMARY OF INVENTION

In accordance with a first aspect of the present invention, an improved X-ray table assembly is provided. The X-ray table assembly includes a table body assembly and table top assembly. The table top assembly, used for supporting a patient under examination is connected to the table body assembly for longitudinal movement relative to the table body assembly. A guard structure for preventing the patient from grasping an end of the table top is mounted to one end of the table end assembly. The guard structure is configured to extend above the table body assembly and beyond the end of the table top assembly and provides a secure structure for the patient to grasp remote from the end of the table top.

In accordance with another aspect of the present invention, an improved table assembly for use in producing images of anatomical structure of a patient under examination is provided. The table assembly comprises a main support structure and a patient support member. Means for movably mounting the patient support to the main support structure are provided. Mounted to at least one end of the support member are means for preventing the inadvertent grasping of the end of the support member by the patient under examination by defining an edge for grasping by the patient remote from the support member end.

In accordance with yet a further aspect of the present invention, an improved table assembly for use in medical diagnostic examination of patients is provided. The table assembly includes a main support structure and a patient support member. The patient support member is movably mounted to the main support structure while maintaining a clearance space therebetween. A shroud means defining a finger placement space remote from the clearance space is mounted to at least one end of the patient support member for discouraging inadvertent placement of patient fingers in the clearance space.

One advantage of the present invention is to provide an improved patient support whereby the likelihood of the patient placing his/her fingers in the space between the table top and table base is substantially reduced.

A further advantage of the present invention is to provide a structure for the patient under examination to grasp which is remote from areas where finger placement could interfere with a moving assembly.

Additional advantages of the present invention will be obtained in reading and understanding the following detailed description of the preferred embodiment and alternate embodiment made in connection with the accompanying drawings.

BRIEF DESCRIPTION OF THE DRAWING

FIG. 6 is a side, detail view of the guard means constructed in accordance with an alternate embodiment of the present invention.

FIG. 7 is a plan view of the guard plate.

FIG. 8A is a plan view of the bottom plate.

FIG. 8B is a side view of the bottom plate.

FIG. 9 is a plan view of the clamp plate.

BEST MODE FOR CARRYING OUT THE INVENTION

Figure 1:
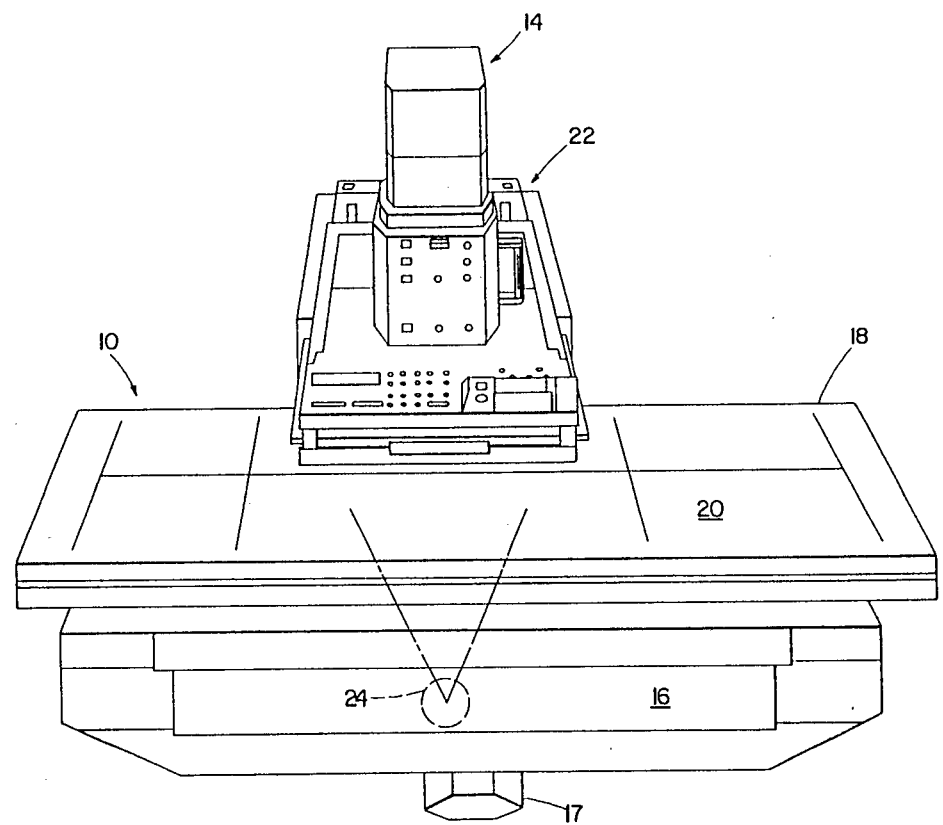
FIG. 1 is a front view of a conventional radiographic and fluoroscopic X-ray system.

FIG. 1 illustrates the overall construction of a prior art medical X-ray apparatus that includes an X-ray table assembly 10, and an imaging system 14. The table assembly 10 includes a table body 16 and a movable table top patient support member 18 that defines a planar patient examining surface 20. The table body 16 is rotatably supported by a main support structure or pedestal, a portion of which is indicated by the reference character 17 and is rotatable about an axis defined by the pedestal 17 between horizontal and vertical positions. The patient support member 18 is supported for longitudinal and transverse movement with respect to the table body 16 in a conventional way.

The imaging system 14 is supported above the patient examining surface 20 by a vertical tower 22. The tower is supported for movement along the table body 16 by a tower support carriage (not shown). A conventional X-ray source 24 (indicated schematically) comprising an X-ray tube and collimator (not shown) is located within the table body 16 and is mounted to the tower carriage. The X-ray source 24, tower 22 and the imaging system 14 move as a unit and thus the longitudinal alignment between the imaging system 14 and the X-ray source 24 is maintained regardless of imaging system position.

Figure 2:
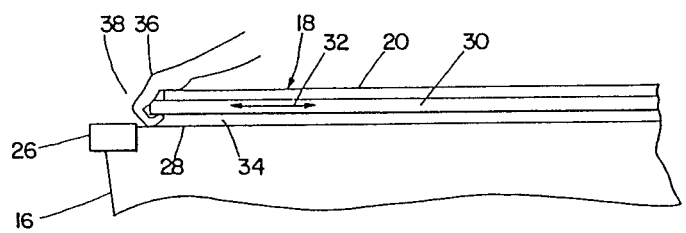
FIG. 2 is a frontal view of a portion of the system shown in FIG. 1.

Referring to FIG. 2, the table top 18 and the table body 16 are shown in more detail. The table body 16 is essentially a hollow metal tub constructed of sheet metal. The X-ray tube 24 and the tower support carriage are located inside the tub. A table body end support 26 is mounted to each end of the table body 16 to provide rigid support for the base structure as well as decorative trim.

To prevent foreign objects or dirt and dust from entering the table body 16 during normal operation, a subtop 28 is provided. The subtop 28 is preferably a thin plastic sheet which completely covers the opening to the inside of the table body 16. The subtop 28 is mounted to a rigid metal frame (not shown) for support and is conveniently placed in position by placing the ends of the subtop frame under the table base end supports 26. Periodic service or maintenance of the components contained in the table body 16 is necessary. In order to gain access to these components, the table top 18 is movable to an extreme longitudinal position and the subtop 28 is removed. The service engineer can them simply reach into the interior of the table body 16 to perform the necessary service.

The table top 18 is comprised of a metal frame 30 and a planar patient examining surface 20. The metal frame 30 is preferably stainless steel and provides for rigid support of the examining surface 20. The planar patient examining surface 20 is made from radiolucent material commonly fiber board covered with plastic laminate. Since the examining surface 20 is in the X-ray beam path, it must exhibit low X-ray attenuation characteristics as well as be homogeneous so not to cause unwanted artifacts in the resultant X-ray image.

As shown by arrows 32, the table top 18 is movable in at least the longitudinal direction with respect to the table body 16. The means for providing the various table top movements are well known in the art and will not be described here.

As described above, in order to insure that table top 18 does not interfere with the table body 16 during table top movement, a clearance space, shown at 34, is provided. This space is sufficiently wide to account for deflections in the table top 18 caused by the weight of the patient but is kept at a minimum to avoid unsightly gaps. Due to tolerances associated with the componentry provided for table top motion, a clearance space in the order of 0.5 inches is typical.

During an examination, a patient is placed on the examining surface 20. The patient may desire to grab hold of a secure structure during patient positioning. Patients have found the end of the table top 18 to be a convenient location to place their hands. The manner in which a patient may place his/her hand 36 is shown at 38. It can be seen that fingers placed around the end of the table top 18 may enter the clearance space 34 and cause interference during table top movement.

Figure 3:
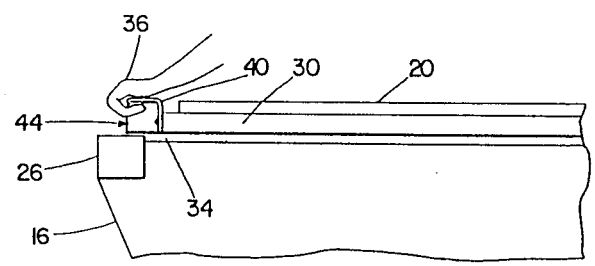
FIG. 3 is a frontal view of a portion of the system shown in FIG. 1 including guard means (shown in cross-section constructed in accordance with the present invention.

Referring now to FIG. 3 the apparatus of the present invention is shown in detail.

Figure 4:
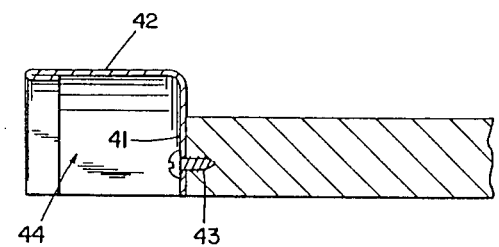
FIG. 4 is a detail, cross-sectional view of the guard means of the preferred embodiment of the present invention.

A guard means 40 is mounted to at least one end of the table top assembly 18. The guard means 40 is preferably 16 gauge stainless steel sheet metal. The width of the guard 40 approximates the width of the table top frame 30. The sheet metal is formed to provide a rigid cowling structure with an inverted "L" shaped cross section (see FIGS. 4 and 5). The "L" shaped structure is defined by a vertical portion 41 and a horizontal portion 42. The height of vertical portion 41 is sufficient to extend the horizontal portion 42 above the clearance space 34 but preferably should not extend above the plane of the examining surface 20. The width of horizontal portion 42 is approximately 2 inches and extends beyond the end of the table top assembly 18. The edge of horizontal portion 42 is rolled over to eliminate any sharpness. The inverted "L" configuration of the guard 40 defines an area or space indicated at 44 which is remote from the clearance space 34.

Figure 5:
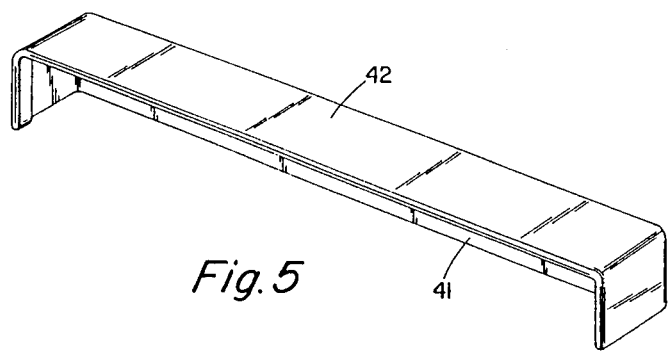
FIG. 5 is a perspective view of the guard means of the preferred embodiment of the present invention.

The guard means 40 is secured to the metal frame 30 at one end of the table top assembly 18 through any one of a number of conventional means such as machine screws 43. Although not necessary for the proper operation of the present invention the ends of the guard means 40 are preferably closed off as shown in FIG. 5.

In operation, a patient is placed on the examining surface 20. The guard means 40 prevents the patient from placing their fingers around the end of table top assembly 18 and into the clearance space 34. Instead, their fingers 36 will grasp the guard means 40 around the end of horizontal portion 42. The patient's fingers 36 will thus extend into space 44 and will not interfere with table body 16 during longitudinal motion of table top assembly 18.

Referring now to FIGS. 6–9, an alternate embodiment of the present invention is shown. A guard assembly 50 is comprised of a guard plate 51, clamp plate 52, bottom plate 53 and a plurality of securing means 54.

The guard assembly 50 is fixedly mounted on the surface of the metal frame 30 at at least one end of the patient examining surface 30. The guard plate 51 is preferably comprised of 0.125" thick semi-rigid urethane. The bottom plate 53 is comprised of stainless steel and is bent upward to an angle of 7°–11° along its midline. The clamp plate 52 is also comprised of stainless steel (0.094" thick) and is mounted between the clamp plate 52 and the bottom plate 53. The entire assembly is secured to the metal frame 30 by a plurality of fasteners 54 preferably #8-32×7/16" flat head machine screws through a plurality of through holes 55, 56, and 57.

When the fasteners 54 are tightened down, the guard plate 51 is forced to conform to the angled shape of bottom plate 53 causing guard plate 51 to extend above the surface and beyond the end of table top 18. This angular extension of guard plate 51 defines an area or space, shown at 66 which is remote to clearance space 34.

The preferred dimensions of guard plate 51, clamp plate 52 and bottom plate 53 are shown in FIGS. 7, 8, and 9.

In operation, as in the earlier described embodiment, a patient is placed on the table top 18. The guard assembly 50 prevents the patient from placing their fingers around the end of the table top assembly 18 and into clearance space 34. Instead, the patient will grasp the guard plate 51. The patient's fingers will extend into space 56 and will not interfere with table base 16 during longitudinal motion of table top assembly 18.

The invention has been described with reference to the preferred embodiment. Obviously, modifications and alterations will occur to others upon reading and understanding the preceding detailed description of the preferred embodiment. It is intended that the invention be construed as including all such alterations and modifications insofar as they come within the scope of the appended claims or equivalents thereof.

Having thus described the preferred embodiment, the invention is now claimed to be:

1. A table assembly for use in medical diagnostic examinations of patients, said table assembly comprising:
   a. a main support structure;
   b. a patient support member defining a planar examining surface having a longitudinal dimension;
   c. means for movably mounting the patient support member to the main support structure for movement along a path substantially parallel to the longitudinal dimension of the patient support member and maintaining a clearance space between said main support structure and said patient support member; and
   d. means for discouraging inadvertent placement of patient fingers in said clearance space, said means comprising a shroud defining a finger placement space remote from said clearance space fixedly attached to said support member, said shroud extending above said clearance space but not substantially above said planar examining surface and further extending beyond the end of said support member.

2. The table assembly of claim 1 wherein said shroud defines an outturned inverted "L" cross-section.

3. An X-ray table assembly for use in creating images of internal structure of a patient under examination, said X-ray table assembly comprising:
   a. a main support structure;
   b. a patient support member defining a longitudinal dimension and a substantially planar examining surface;
   c. means for movably mounting the patient support member to the main support structure for motion along an axis substantially parallel to said longitudinal dimension; and
   d. guard means for preventing inadvertent grasping of an end of the support member by the patient under examination, said guard means fixedly mounted to one end of the support member and defining a patient grasping edge positioned above the main support structure and extending beyond the end of the patient support member wherein said patient grasping edge is further positioned to lie within a plane substantially coplanar to the planar examining surface of said patient support member.

4. An X-ray table assembly comprising a movable X-ray table top defining a substantially planar surface for supporting a patient under examination and a guard for prevention of inadvertent placement of patient fingers around the end of said movable table top wherein said guard comprises a shroud fixedly mounted to one end of the movable x-ray table top, said shroud having a horizontal extension and a vertical extension defining a space for finger placement remote to the end of the table top; and wherein the vertical extension of said shroud does not extend substantially beyond the planar surface of said table top.

5. A table assembly for use in creating radiographic images of patients under examination comprising:
   a. a table base;

b. a table top having a substantially planar patient examining surface;
c. means for mounting the table top to the table base; and
d. a guard structure mounted to at least one end of the table top for preventing placement of patient fingers around the table top end, said guard structure comprising a vertical portion extending perpendicularly from the table top end and a horizontal portion perpendicular to said vertical portion and extending outward from said table top end, said horizontal portion substantially coplanar to said patient examining surface.

* * * * *